United States Patent [19]

Kannan

[11] Patent Number: 4,874,894

[45] Date of Patent: Oct. 17, 1989

[54] PROCESS FOR THE PRODUCTION OF BENZENESULFONAMIDES

[75] Inventor: Ramamurthi Kannan, Edgewood, Ky.

[73] Assignee: Hilton Davis Co., Cincinnati, Ohio

[21] Appl. No.: 43,788

[22] Filed: Apr. 29, 1987

[51] Int. Cl.$^4$ .......................................... C07C 143/882
[52] U.S. Cl. ......................................... 564/93; 564/90; 562/828; 562/833
[58] Field of Search ................ 564/90, 93; 260/543 R

[56] References Cited

PUBLICATIONS

CA62: 11023c Chem. Pharm. Bull. (Tokyo) 12(2) 1451-7 (1964).
Ernest H. Huntress and Frederick H. Carten J. Am. Chem. Soc. 62, pp. 511–514 (1940) Identification of Organic Compounds I. Chlorosulfonic Acid as a Reagent for the Identification of Aryl Halides.
Ernest H. Huntress and Frederick H. Carten J. Am. Chem. Soc. 62 pp. 603–604 (1940) Identification of Organic Compounds III. Chlorosulfonic Acid as a Reagent for the Characterization of Aromatic Ether.
Marcus S. Morgan and Leonard H. Cretcher J. Am. Chem. Soc. 70, pp. 375–378 (1948) A Kinetic Study of Alkylation by Ethyl Arylsulfonates.

*Primary Examiner*—Paul J. Killos
*Attorney, Agent, or Firm*—Terrence E. Miesle

[57] ABSTRACT

Process comprises the combination of two steps of interacting a R-benzene, sulfuric acid and phosphorus oxychloride to obtain 4-R-benzenesulfonyl chloride and amidating said sulfonyl chloride to produce 4-R-benzenesulfonamide.

7 Claims, No Drawings

PROCESS FOR THE PRODUCTION OF BENZENESULFONAMIDES

BACKGROUND OF THE INVENTION (a) Field of the Invention

This invention relates to a novel two-step process for the preparation of 4-substituted benzenesulfonamides useful in the art of hot melt jet printing ink vehicles and to a novel process for the preparation of 4-substituted benzenesulfonyl chloride intermediates to said benzenesulfonamides.

(b) Description of the Prior Art

It is well established in the art that substituted benzenesulfonyl chlorides are normally prepared by interacting a substituted benzene with at least two molar equivalents of chlorosulfonic acid. This reaction in many instances results in poor yields of the desired product because the equilibrium concentration of the chlorosulfonic acid tends to form poly substitution if the substitutent on the benzene is reactive, or one which activates the ring. Moreover, with substitutents such as alkyl groups, there exists competing reactions to substitute in the position ortho or para to the alkyl group. In many instances this will result in mixtures of products or in the majority of the product being the undesired isomer. Furthermore, the use of chlorosulfonic acid as the reaction medium also results in a competing reaction in which a sulfone is produced as a result of the interaction of the chlorosulfonic acid and two molecular equivalents of the substituted benzene. In addition, the reaction utilizing chlorosulfonic acid is generally practiced using an inert solvent to dilute the reactants. The preparation of the benzenesulfonamides are generally obtained by treating the benzenesulfonyl chloride with concentrated ammonium hydroxide in an aqueous solution. Although, the conversion of the benzenesulfonyl chloride to the benzenesulfonamide is generally quantitative, the combined overall yield using chlorosulfonic acid in the first step is generally in the range of fifty to seventy percent.

The following items to date appear to constitute the most relevant prior art with regard to the instant invention.

Huntress and Carten in the Journal of the American Chemical Society, Volume 62 (1940) pages 511 to 514 published an article entitled "Identification of Organic Compounds I. Chlorosulfonic Acid as a Reagent for the Identification of Aryl Halides". This article describes the preparation of twenty-four halogenated benzenesulfonyl chlorides and four halogenated naphthalenesulfonyl chlorides frim the corresponding halogenated aromatic hydrocarbon and a relatively large excess of chlorosulfonic acid both with an inert solvent and with no solvent. It further describes the preparation of the corresponding arylsulfonamide by reacting the sulfonyl chloride with ammonia or ammonium carbonate.

Huntress and Carten in the Journal of the American Chemical Society, Volume 62 (1940) pages 603 and 604 published an article entitled "Identification of Organic Compounds .III. Chlorosulfonic Acid as a Reagent for the Characterization of Aromatic Ethers". In this article the authors describe the preparation of arylsulfonamides via arylsulfonyl chlorides prepared by the interaction of aromatic hydrocarbons with chlorosulfonic acid using the procedure described in the preceeding reference. They describe the results of chlorosulfonating thirty-six aromatic ethers.

Morgan and Cretcher in the Journal of the American Chemical Society, Volume 70 (1948) pages 375 to 378 published an article entitled "A Kinetic Study of Alkylation by Ethyl Arylsulfonates". The authors describe a process for the preparation of 4-methoxybenzenesulfonyl chloride by interacting anisole and chlorosulfonic acid obtaining the desired product in a sixty-six percent yield.

SUMMARY OF THE INVENTION

In one of its process aspects, the invention relates to a two-step process for producing 4-R-benzenesulfonamides which comprises interacting in the first step a R-benzene, sulfuric acid and phosphorus oxychloride to obtain 4-R-benzenesulfonyl chloride which is amidated in the second step to obtain 4-R-benzenesulfonamide.

In a second of its process aspects, the invention relates to a process for producing a 4-R-benzenesulfonyl chloride which comprises interacting a R-benzene, sulfuric acid and phosphorus oxychloride to obtain said 4-R-benzenesulfonyl chloride.

DETAILED DESCRIPTION INCLUSIVE OF THE PREFERRED EMBODIMENTS

More specifically, this invention in one of its process aspects resides in the novel process for the preparation of a 4-R-benzenesulfonamide of the formula

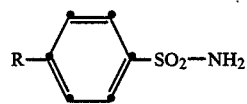

FORMULA I wherein R represents a non-tertiary $C_1$ to $C_{16}$ alkyl or a non-tertiary $C_1$ to $C_{16}$ alkoxy, which consists of in the first step reacting a R-benzene with sulfuric acid and phosphorus oxychloride to produce a 4-R-benzenesulfonyl chloride of the formula

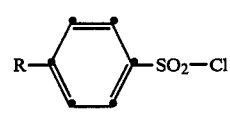

FORMULA II and in a second step amidating said 4-R-benzenesulfonyl chloride with ammonia in an aqueous medium to obtain said 4-R-benzenesulfonamide.

In a first particular embodiment in accordance within its first process aspect, the invention sought to be patented resides in the novel process for preparing a 4-R-benzenesulfonamide of Formula I wherein R represents non-tertiary $C_1$ to $C_{16}$ alkoxy.

In a second particular embodiment in accordance within its first process aspect, the invention sought to be patented resides in the novel process for preparing a 4-R-benzenesulfonamide of Formula I wherein R represents a non-tertiary $C_1$ to $C_{16}$ alkyl.

This invention, in its second process aspect, resides in the process for preparing 4-R-benzenesulfonyl chloride of the formula

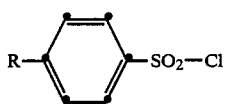

FORMULA II wherein R represents a non-tertiary $C_1$ to $C_{16}$ alkyl or a non-tertiary $C_1$ to $C_{16}$ alkoxy which consists of reacting a R-benzene with sulfuric acid and phosphorus oxychloride to produce a 4-R-benzenesulfonyl chloride.

In a first particular embodiment in accordance within its second process aspect, the invention sought to be patented resides in the novel process for preparing a 4-R-benzenesulfonyl chloride of Formula II wherein R represents non-tertiary $C_1$ to $C_{16}$ alkyl.

In a second particular embodiment in accordance within its second process aspect, the invention sought to be patented resides in the novel process for perparing a 4-R-benzenesulfonyl chloride of Formula II wherein R represents non-tertiary $C_1$ to $C_{16}$ alkyl.

As used herein the term "non-teritary $C_1$ to $C_{16}$ alkyl" denotes saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl, n-tridecyl, n-tertadecyl, n-pentadecyl, n-hexadecyl, 1,3,5-trimethylhexyl, 1,5-dimethyl-4-ethylhexyl, 5-methyl-2-butyl-hexyl, 2-propylnonyl, 2-butyloctyl, 2-pentylnonyl, and the like.

The term "non-teritary $C_1$ to $C_{16}$" alkoxy includes saturated, acyclic, straight or branch-chained groups such as methoxy, ethoxy, propoxy, isopropoxy, butoxy, sec-butoxy, isobutoxy, pentoxy, hexoxy, heptoxy, octoxy, nonoxy, decoxy, undecoxy dodecoxy, tetradeoxy, hexadecoxy and the like.

The processes of this invention afford a novel convenient and economically advantageous synthetic route to a large number of 4-R-benzenesulfonamides of the type represented by Formula I. Many species defined by Formula I are known in the prior art as being useful as components in hot melt ink systems for jet ink printing.

The processes of this invention also afford 4-R-benzenesulfonyl chlorides of Formula II which are primarily useful as intermediates to the sulfonamides depicted by Formula I.

It has been found that the novel processes of this invention produces 4-R-benzenesulfonyl chlorides and the corresponding benzenesulfonamides in high yields with only small amounts of the 2-isomer and very little formation of the sulfone. This is surprising in view of the reports in the prior art that the competing reactions for the formation of the ortho isomer and the sulfone result in substantial amounts of the undesired ortho isomer and sulfone when prepared by the known processes to obtain the desired para-benzenesulfonyl chlorides and corresponding sulfonamides.

The process of the instant invention for the preparation of the 4-R-benzenesulfonyl chlorides and 4-R-benzenesulfonamides has the advantages over the previously known processes for the preparation of these compounds. One advantage of this process is that it is run with less stringent temperature control, that is, the reaction temperature does not have to be maintained at very low temperatures. Another advantage which results in economic production and capital savings is that there are fewer by-products formed, thus, obtaining purer products which use less expensive purification methods to purify the products of the instant processes. Still another advantage over the prior art processes is that the instant process for the preparation of the sulfonyl chlorides is much easier to control because it does not produce the exotherm that the prior art processes exhibit.

The best mode contemplated by the inventors of carrying out this invention will now be described so as to enable any person skilled in the art to which it pertains to make and use the same.

In accordance with the first of the aforementioned process aspects of this invention, the 4-R-benzenesulfonyl chlorides are obtained by reacting in the first step a R-benzene with approximately an equimolar amount to a ten percent excess of phosphorus oxychloride and a molar excess of from approximately three percent to approximately fifteen percent sulfuric acid. This reaction is conveniently carried out by adding the phosphorus oxychloride to the subsituted benzene and slowly adding the sulfuric acid at a temperature in the range of zero to approximately 90° C.

Alternatively the R-benzene can be added to a mixture of sulfuric acid and phosphorus oxychloride. The resulting reaction mixture is maintained at a temperature in the range of 50° to 95° C. for a period of approximately one hour to approximately twenty-four hours. Optionally, sodium chloride can be added to the reaction mixture prior to the holding time. The 4-R-benzenesulfonyl chlorides of Formula II can be isolated by pouring the reaction mixture onto a mixture of ice and water and filtering the desired sulfonyl chloride.

The 4-R-benzenesulfonamides of Formula I are obtained by reacting the corresponding 4-R-benzenesulfonyl chlorides of Formula II with ammonium hydroxide. The reaction is conveniently carried out in water at a temperature in the range of forty and ninety-five degrees for a period of time from thirty minutes to twenty four hours. The isolated sulfonamides can be purifed by conventional means such as trituration, recrystallization or reslurrying with suitable organic liquid or by dissolving in a suitable alkali, optionally treating the solution with a decoloring carbon, filtering and reprecipitating by adding a dilute acid solution.

Alternatively, instead of isolating the 4-R-benzenesulfonyl chlorides of Formula II, the reaction mixture containing the sulfonyl chlorides can be poured onto a mixture of ammonium hydroxide, ice and water and treated in the same manner as directly above to obtain the desired 4-R-benzenesulfonamide of Formula II.

The R-benzenes required as starting materials in the preparation of the sulfonamides of Formula I and the sulfonyl chlorides of Formula II form an old and well known class of compounds readily obtained from commercial sources.

The compounds prepared by the processes of this invention form a part of a large and well known class of compounds. The molecular structures of the compounds made by the processes of this invention were assigned on the basis of the study of their infrared and nuclear magnetic resonance spectra in conjunction with the spectra of compounds prepared by the art described methods.

The following examples will further illustrate the invention without, however, limiting it thereto. All melting paints are uncorrected.

EXAMPLE 1

A. With stirring, 51.5 g (0.525 m) of 100 percent sulfuric acid was added to a mixture of 54.0 g (0.5 m) of anisole and 46.0 ml (0.5 m) of phosphorus oxychloride allowing the temperature to rise to approximately 45 C. during the addition. While attempting to maintain approximately 45° C. the temperature slowly rose to approximately 53° C. after about two hours. After stirring overnight at ambient temperature, 6.0 g of sodium chloride was added and the resulting mixture was heated to and maintained at approximately 90° for about four hours. The reaction mixture was cooled and poured onto a mixture of 500.0 g ice, 250.0 ml of water and 30.0 g of sodium chloride. The solid which formed was collected by filtration, washed with cold water and dried to obtain 96.5 g of 4-methoxybenzenesulfonyl chloride a gray-white solid. The nuclear magnetic resonance spectrum was in accord with the desired product.

B. With stirring 96.47 g (0.467 m) of the 4-methoxybenzenesulfonyl chloride obtained in part A above was slowly added to a slurry of 175.0 ml of concentrated ammonium hydroxide and 175.0 g of ice keeping the temperature under −5° C. during the addition. Slowly the resulting mixture was heated to approximately 70° C. over approximately two and one half hours. The resulting slurry was cooled and maintained at approximately 10° C. for about forty minutes. The solid was collected by filtration, washed three times with 50.0 ml of ice water and dried on the filter to obtain 97.37 g of water-wet 4-methoxybenzenesulfonamide. This product was suspended in 664.0 ml of water and 22.0 ml of 50 percent aqueous sodium hydroxide and 3.75 g of decolorizing carbon was added. After approximately forty-five minutes, the carbon was collected by filtration and washed twice with 50.0 ml of water. The filtrate and 50.0 ml or rinse water was adjusted to approximately pH 3 with the addition of approximately 33.0 ml of concentrated hydrochloric acid. The resulting slurry was cooled to approximately 5° C., stirred approximately two hours and the solid was collected by filtration, washed three times each with 50.0 ml of ice water and dried in vacuo to obtain 70.93 g of 4-methoxybenzenesulfonamide, a shiny white solid which melted at 111.5°–112.50° C. The nuclear magnetic resonance spectrum was concordant with the assisgned structure.

EXAMPLE 2

To a mixture of 54.0 g (0.5 m) of anisole, 46.0 ml (0.5 m) of phosphorus oxychloride cooled to about 17° C., there was added slowly 51 g (0.525 m) of 100 percent sulfuric acid allowing the temperature to rise to approximately 29° C. at which temperature an external water bath was applied lowering the temperature to approximately 17° C. When the addition was complete, the water bath was removed and the temperature of the reaction mixture gradually rose to about 27° C. over approximately one hour and forty-five minutes. The reaction mixture was stirred overnight at ambient temperature. To the reaction mixture, 6.02 g of sodium chloride was added and the resulting mixture was heated to approximately 90° C. After approximately three and one half hours at about 90° C., the reaction mixture was cooled and poured slowly into a slurry of 500.0 g ice, 250.0 ml water and 41.6 g of sodium chloride. The solid which formed was collected by filtration, washed three times, each with 50.0 ml ice water and dried on the filter to obtain 94.9 g of 4-methoxybenzenesulfonyl chloride, a pink-white solid. The nuclear magnetic resonance spectrum was concordant with the assigned structure.

B. Following the procedure described in Example 1, part B above, 94.94 g (0.45 m) of 4-methoxybenzenesulfonyl chloride from part A above was interacted with ammonium hydroxide to obtain 70.41 g of 4-methoxybenzenesulfonamide, shiny white crystals which melted at 111°–112° C.

EXAMPLE 3

A. With stirring 51.5 g (0.525 m) of 100 percent sulfuric acid was added to a mixture of 54.0 g (0.5 m) of anisole and 46.0 ml (0.5 m) of phosphorus oxychloride maintaining a temperature of less than 5° C. by means of an ice-water bath. The ice-water bath was removed and the reaction mixture was allowed to warm to approximately 29° C. over approximately ninety minutes. Over approximately twenty minutes, the reaction mixture was heated to about 95° C. and maintained approximately two hours. After cooling the reaction mixture was poured slowly into a mixture of 501.0 g ice, 250.0 ml water and 31.0 g of sodium chloride keeping the temperature under 11° C. The resulting solid was collected by filtration, washed three times, each with 50.0 ml of ice water and dried to obtain 103.25 g of 4-methoxybenzenesulfonyl chloride, a pink-white solid. The nuclear magnetic resonance spectrum was in accord with the assigned structures.

B. Proceeding in a manner similar to that described in Example 1, part B above, 100.42 g (0.486 m) of 4-methoxybenzenesulfonyl chloride from part A above was interacted with ammonium hydroxide and acidified to obtain 69.25 g of 4-methoxybenzenesulfonamide, a white solid which melted at 111.5°–112.5° C. The nuclear magnetic resonance spectrum was in accord with the assigned structure.

EXAMPLE 4

A. With stirring, 929.0 g phosphorus oxychloride was added to 836.0 g ethylbenzene. The resulting mixture was heated to approximately 69° C. and 599.0 g of 100 percent sulfuric acid was added over approximately sixteen minutes with the temperature rising to approximately 78° C. and it continued to slowly rise over approximately thirty-seven minutes to approximately 84° C. The mixture was held at approximately 80° C. for about two hours and then maintained at approximately 90° C. for an additional three hours. After cooling to approximately 82° C. the reaction mixture was poured slowly onto a mixture of 1500.0 ml water and 1500.0 g ice keeping the temperature under 5° C. with the addition of 440.0 g ice. After approximately ten minutes of stirring, the agitation was stopped and the mixture separated into two layers. The lower layer containing the product was separated and immediately poured onto 500.0 g of ice and 3500.0 ml of ice water was added. After approximately twenty minutes of stirring, the layers were separated to obtain 1400.0 ml of 4-ethylbenzenesulfonyl chloride.

B. Slowly the 1400.0 ml of 4-ethylbenzenesulfonyl chloride was added over twenty-seven minutes to a solution of 1164.0 ml of 28 percent ammonium hydroxide and 1000.0 ml of tap water keeping the temperature under 30° C. by means of external cooling. After stirring the resulting mixture approximately ten minutes at approximately 30° C., it was gradually heated over approximately forty minutes to approximately 70° C. and maintained about one hour. The resulting slurry was allowed to stir overnight at ambient temperature. The mixture was cooled to approximately 15° C. for about one hour and the solid was collected by filtration, washed six times each with 1000.0 ml of tap water and dried on the filter for approximately four hours to obtain 859.0 g of water-wet solid which contained 834.0 g of 4-ethylbenzenesulfonamide.

C. With stirring 120.0 g of the water-wet solid from part B above was suspended in 400.0 g of denatured ethyl alcohol and the mixture was heated to approximately 50° C. where the solid dissolved. To the solution, 5.0 g of decolorizing carbon was added and the resulting mixture was stirred approximately thirty minutes and the carbon was collected by filtration. To the filtrate 200.0 ml of deionized water and 100.0 ml of ethyl alcohol was added and the resulting mixture was heated to approximately 70° C. to effect complete solution. The solution was cooled to approximately 20° C. over approximately thirty minutes, stirred about fifteen minutes under 20° C. and the solid which formed was collected by filtration, washed six times each with 250.0 ml of deionized water and dried to obtain 100.0 grams of 4-ethylbenzenesulfonamide, white solid which melted at 104°–107.5° C.

EXAMPLE 5

A. A mixture of 53.08 g (0.5 m) of ethylbenzene and 46.0 ml (0.5 m) of phosphorus oxychloride was heated to approximately 50° C. and 51.5 g (0.525 m) of 100 percent sulfuric acid was added slowly keeping the temperature in the range of 60° to 66° C. by adjusting the rate of addition. The reaction mixture was maintained at approximately 60° C. for approximately twenty-two and one-half hours and then maintained at about 90° C. for approximately five hours. After cooling, the reaction mixture was poured onto a slurry of 600.0 g of ice and 200.0 ml of water. After approximately forty-five minutes of stirring, the agitation was stopped and the layers separated. The lower layer containing the 4-ethylbenzenesulfonyl chloride was separated and washed with about 500 ml of cold water and separated. The upper water layer and the water wash were discarded. The oil organic liquid layer of 4-ethylbenzenesulfonyl chloride was added slowly to a slurry of 200.0 g of ice and 200.0 ml of concentrated ammonium hydroxide. The resulting mixture was stirred approximately thirty minutes at about 40° C. and then stirred overnight at ambient temperature. The solid was collected by filtration, washed with cold water and dried to obtain 81.71 g of 4-ethylbenzenesulfonamide, a white solid which melted at 107°–109° C.

B. The solid from part A above was suspended in 730.0 ml of water and 37.0 g of 50 percent aqueous sodium hydroxide was added and the resulting mixture was stirred approximately forty-five minutes. To the mixture 4.0 g of decolorizing carbon was added and after approximately forty-five minutes, the carbon was collected by filtration and washed with 100.0 ml of water. The filtrate was made acid with the addition of 37.0 ml of concentrate hydrochloric acid, cooled, the solid collected by filtration, the solid washed with water and dried to obtain 78.3 g of 4-ethylbenzenesulfonamide, a white solid which melted at 107° to 108.5° C. The nuclear magnetic resonance spectrum was in accord with the assigned structure.

EXAMPLE 6

To a mixture of 612.0 g (3.0 m) of nonylbenzene and 465.0 g (3.03 m) of phosphorus oxychloride, 300.0 g (3.06 m) of 100 percent sulfuric acid was added over approximately twenty minutes maintaining a temperature in the range of 70° to 75° C. by the rate of addition. The resulting reaction mixture was stirred at approximately 80° C. for about two hours and at approximately 90° C. for about two hours. The mixture was cooled to approximately 80° C. and slowly it was added to a solution of 580.0 ml of 28 percent ammonium hydroxide and 500.0 ml of water. A small portion of the reaction mixture was discarded because it became overheated while adding the first portion. The resulting mixture was heated to approximately 80° C., maintained about fifteen minutes and 100.0 g of decolorizing carbon was added. After about fifteen minutes, 30.0 g of cellulose filter-aid was added and the carbon was collected by filtration, however, the filtration stopped after approximately half of the mixture was filtered. The filter cake was washed with hot isopropyl alcohol. The second portion was filtered using a steam jacketed filter funnel with a diatomateous earth precoating on the filter. The solid which formed in the filtrate upon its sitting overnight was very thick and to make a stirrable slurry water and ice was added. The solid was collected by filtration and washed with deionized water. The filter cake was divided into two portions.

B. The first portion was reslurried in the deionized water, filtered, washed with deionized water and dried to obtain 219.0 g of off white solid which contained particles of a gray solid. The 219.0 g of solid was dissolved in 150.0 ml of hot isopropyl alcohol and 29.0 g of decolorizing carbon was added. After thirty minutes of stirring, the carbon was collected by filtration on a filter coated with diatomateous earth and the filter cake was washed twice, each time with 100.0 ml of hot isopropyl alcohol. The solid which formed in the filtrate upon cooling was collected by filtration and dried to obtain 148.0 g of 4-nonylbenzenesulfonamide, a white solid which melted at 94.55° to 95.2° C.

C. The second portion was dissolved in 300.0 ml of hot isopropyl alcohol and 31.0 g of decolorizing carbon was added. The carbon was collected by filtration. The filtrate was cooled and water and ice was added to the resulting slurry. The solid in the slurry was collected by filtration and dried to obtain 135.0 g of 4-nonylbenezenesulfonamide, a white solid which melted at 94.5° to 95.1° C.

EXAMPLE 7

A. A mixture of 59.0 ml (1.1 m) of 100 percent sulfuric acid and 102.5 ml (1.1 m) of phosphorus oxychloride was heated to approximately 80° C. and 135.0 g (1.0 m) of butylbenzene was added slowly over approximately 25 minutes maintaining approximately 80° C. by the rate of addition. The resulting reaction mixture was stirred about one hour at approximately 80° C., approximately one hour at approximately 85° C. and about two hours at approximately 94° C.

The reaction mixture was cooled slightly and poured into a mixture of 300.0 ml of 28 percent ammonium hydroxide and ice. The resulting slurry was heated to a temperature in the range of 80° to 85° C. and maintained for approximately thirty minutes and at approximately 95° C. for about thirty minutes. The resulting mixture was cooled to abut 60° C. with the addition of ice and 380.0 ml of isopropanol was added. The reaction mixture was cooled to 20° C. and 3000.0 ml of ice water was added slowly and the resulting mixture was cooled to approximately 5° C. and stirred for one hour. The solid which formed was collected by filtration, washed with ice water and dried on the filter over the weekend to obtain 195.5 g of 4-butylbenzenesulfonamide, a pale brown solid.

B. The 195.5 g of 4-butylbenzenesulfonamide from part A above was dissolved in 300.0 ml of isopropyl alcohol at a temperature in the range of 50° to 60° C. and 29.0 g of decolorizing charcoal was added. After stirring for approximately two hours, the carbon was collected by filtration washing the carbon filter cake three times each with 50.0 ml of hot isopropyl alcohol. The filtrate was heated and 1.0 liter of deionized water was added. Heating continued until solution was complete. The solution was cooled slowly to 25° C. and slowly 3500.0 ml of ice and water was added and cooling continued. The resulting slurry was stirred at approximately 5° C. for about one hour and the solid was collected by filtration and dried on the filter to obtain 174.9 g of 4-butylbenzenesulfonamide, a pale cream colored solid which melted at 92°-94° C.

EXAMPLE 8

To a mixture of 53.6 g (0.5 m) of ethylbenezene and 50.4 ml (0.54 m) of phosphorus oxychloride heated to approximately 80° C., 51.75 g (0.523 m) of 99.34 percent sulfuric acid was slowly added over approximately four hours maintaining approximately 80° C. After stirring an additional two hours at approximately 80° C., the reaction mixture was heated to about 90° C. and maintained at about 90° C. for approximately two hours. After cooling, the reaction mixture was poured slowly onto a slurry of 600.0 g ice and 200.0 ml water. To the stirring mixture 600.0 ml of toluene was added. After approximately twenty minutes the agitation was stopped and the layers separated. The organic layer was washed first with 200.0 ml of ice water and separated and then with 50.0 ml of saturated aqueous sodium chloride solution. The organic layer was dried by mixing the anhydrous calcium chloride and filtered. The organic layer was concentrated by evaporation of the toluene under vacuum to obtain 116.1 g of a tan oil which was analyzed by gas chromatographic analysis to contain 28.6 percent toluene, 65.4 percent 4-ethylbenzenesulfonyl chloride and 3.4 percent 2-ethylbenzenesulfonyl chloride.

COMPARATIVE EXAMPLE

With stirring 122.0 ml (1.0 m) of ethylbenzene was added slowly to 198.0 ml (3.0 m) of chlorosulfonic acid which had been cooled to approximately −10° C. in an ice-salt bath. The addition was difficult to control with the gas evolution but was completed in approximately two hours. The reaction mixture was stirred overnight at ambient temperature. The mixture was poured onto ice and 1.25 l of toulene was added. The toluene layer was separated, washed with ice water and separated. The resulting organic layer was concentrated by evaporating the toluene at reduced pressure resulting in 158.5 g of light brown oil. A vacuum fractional distillation of 130.27 g of the oil produced 108.1 g of pale yellow oil collected between 105° and 112° C. at approximately 0.35 mm of mercury. Gas chromatagraphic analysis of this oil indicated that it was 5.4 percent toluene, 45.7 percent 4-ethylbenzene-sulfonyl chloride, 27.8 percent 2-ethylbenzenesulfonyl chloride and 21.1 percent unknowns.

It is contemplated that by following procedures similar to those described in the foregoing examples but interacting the appropriate R-benzenes with sulfuric acid and phosphorus oxychloride there will be obtained the following 4-R-benzenesulfonyl chlorides of Formula II and subsequent reaction with ammonium hydroxide will result in the corresponding 4-R-benzenesulfonamides of Formula I. 4-ethoxybenzenesulfonyl chloride, 4-propyloxybenzenesulfonyl chloride, 4-isopropoxybenzenesulfonyl chloride, 4-butoxybenzene sulfonyl chloride, 4-isobutoxybenzenesulfonyl chloride, 4-pentoxybenzenesulfonyl chloride, 4-hexoxybenzenesulfonyl chloride, 4-heptoxybenzenesulfonyl chloride, 4-octoxybenzenesulfonyl chloride, 4-isooctoybenzenesulfonyl chloride, 4-nonoxybenzenesulfonyl chloride, 4-decoxybenzenesulfonyl chloride, 4-undecoxybenzene sulfonyl chloride, 4-dodecoxybenzenesulfonyl chloride, 4-tridecoxybenzenesulfonyl chloride, 4-tetradecoxybenzenesulfonyl chloride, 4-pentadecoxybenzenesulfonyl chloride, 4-hexadecoxybenzenesulfonyl chloride, 4-propylbenzenesulfonyl chloride, 4-isopropylbenzenesulfonyl chloride, 4-isobutylbenzenesulfonyl chloride, 4-pentylbenzenesulfonyl chloride, 4-isopentylbenzenesulfonyl chloride, 4-hexylbenzenesulfonyl chloride, 4-isohexylbenzenesulfonyl chloride, 4-heptylbenzenesulfonyl chloride, 4-octylbenzenesulfonyl chloride, 4-isooctylbenzenesulfonyl chloride, 4-decylbenzenesulfonyl chloride, 4-undecylbenzenesulfonyl chloride, 4-dodecylbenzenesulfonyl chloride, 4-tridecylbenzenesulfonyl chloride, 4-tetradecylbenzenesulfonyl chloride, 4-pentadecylbenzenesulfonyl chloride, 4-hexadcylbenzenesulfonyl chloride.

What is claimed is:

1. A process for the production of a 4-R-benzenesulfonamide of the formula

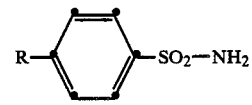

wherein R represents a non-tertiary $C_1$ to $C_{16}$ alkyl or a non-tertiary $C_1$ to $C_{16}$ alkoxy, which consists of in the first step reacting a R-benzene with sulfuric acid and phosphorus oxychloride to produce a 4-R-benzenesulfonyl chloride of the formula

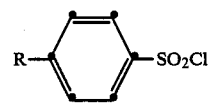

and in a second step amidating said 4-R-benzenesulfonyl chloride with ammonia in an aqueous medium to obtain said 4-R-benzenesulfonamide.

2. A process according to claim 1 for preparing a 4-R-benzenesulfonamide wherein R represents a non-tertiary $C_1$ to $C_{16}$ alkoxy.

3. A process according to claim 2 for preparing 4-methoxybenzenesulfonamide.

4. A process according to claim 1 for preparing a 4-R-benzensulfonamide wherein R represents a non-tertiary $C_1$ to $C_{16}$ alkyl.

5. A process according to claim 4 for preparing 4-ethylbenzenesulfonamide.

6. A process according to claim 4 for preparing 4-butylbenzenesulfonamide.

7. A process according to claim 4 for preparing 4-nonylbenzenesulfonamide.

* * * * *